UNITED STATES PATENT OFFICE.

ALEX B. DAVIS, OF CINCINNATI, OHIO, ASSIGNOR TO THE ELI LILLY AND COMPANY, OF INDIANAPOLIS, INDIANA, A CORPORATION OF INDIANA.

COMPOUNDS OF CINCHONA ALKALOIDS AND 2-PHENYL-QUINOLIN-4-CARBOXYLIC ACID.

15,127. Specification of Reissued Letters Patent. Reissued June 21, 1921.

No Drawing. Original No. 1,213,464, dated January 23, 1917, Serial No. 102,310, filed June 7, 1916. Application for reissue filed May 5, 1921. Serial No. 468,142.

*To all whom it may concern:*

Be it known that I, ALEX B. DAVIS, a citizen of the United States, residing at Cincinnati, Hamilton county, and State of Ohio, (formerly a resident of Indianapolis, Indiana,) have invented and discovered certain new and useful Improvements in Compounds of Cinchona Alkaloids and 2-Phenyl-Quinolin-4-Carboxylic Acid, of which the following is a specification.

The invention relates to a combination of a cinchona alkaloid, particularly quinin, with 2-phenyl-quinolin-4-carboxylic acid. It is of value in medicine as an antipyretic, antiphlogistic and uric acid eliminant.

The compound is made by adding a solution of a salt of quinin or other cinchona alkaloid to a solution of an alkali salt of 2-phenyl-quinolin-4-carboxylic acid.

In detail the process may be carried out as follows: 137 grams of quinin bisulfate $C_{20}H_{24}N_2O_2—H_2SO_4.7H_2O$ are dissolved in nine-hundred c. c. of water at 35° C., and into this is quickly poured with stirring a solution of 124.5 grams of 2-phenyl-quinolin-4-carboxylic acid in 800 c. c. of water and just sufficient caustic soda to neutralize it. The quinin-compound quickly separates as a sticky mass which quickly solidifies to a mass of crystals. The mass is broken up, filtered from the water, washed with water and dried at a low temperature, when it appears as a nearly tasteless white, crystalline powder, almost insoluble in water, decomposed by alkalis, soluble in hot acetone and alcohol.

What I claim is:

1. A compound of a cinchona alkaloid and 2-phenyl-quinolin-4-carboxylic acid.

2. A compound of quinin and 2-phenyl-quinolin-4-carboxylic acid.

In witness whereof, I have hereunto set my hand at Cincinnati, Ohio, this 14th day of April, 1921.

ALEX B. DAVIS.

Witnesses:
P. G. GROVES,
EMILY F. SPENER.